(12) United States Patent
Kecman

(10) Patent No.: US 8,690,767 B2
(45) Date of Patent: Apr. 8, 2014

(54) SPECULUM

(75) Inventor: Maja Kecman, London (GB)

(73) Assignee: Speculus (UK) Limited, Liverpool (GB)

( * ) Notice: Subject to any disclaimer, the term of this patent is extended or adjusted under 35 U.S.C. 154(b) by 642 days.

(21) Appl. No.: 11/993,577

(22) PCT Filed: Jun. 22, 2006

(86) PCT No.: PCT/GB2006/002310
§ 371 (c)(1),
(2), (4) Date: Sep. 15, 2009

(87) PCT Pub. No.: WO2006/136844
PCT Pub. Date: Dec. 28, 2006

(65) Prior Publication Data
US 2010/0076344 A1    Mar. 25, 2010

(30) Foreign Application Priority Data
Jun. 22, 2005 (EP) .................................. 05253889

(51) Int. Cl.
*A61B 1/32* (2006.01)
(52) U.S. Cl.
USPC .......................................................... 600/222
(58) Field of Classification Search
USPC .................................... 600/220–225
See application file for complete search history.

(56) References Cited

U.S. PATENT DOCUMENTS

| | | | |
|---|---|---|---|
| 2,083,573 A * | 6/1937 | Morgan | ......................... 600/224 |
| 3,985,125 A | 10/1976 | Rose | |
| 4,130,113 A * | 12/1978 | Graham | ......................... 600/224 |
| 4,227,537 A | 10/1980 | Suciu | |
| 4,448,205 A | 5/1984 | Stenkvist | |
| 4,800,896 A | 1/1989 | Jalowayski | |
| 4,807,600 A * | 2/1989 | Hayes | ........................... 600/203 |
| 4,905,670 A * | 3/1990 | Adair | ............................ 600/104 |
| 5,143,054 A * | 9/1992 | Adair | ............................ 600/104 |
| 5,458,595 A * | 10/1995 | Tadir et al. | ...................... 606/15 |
| 5,499,964 A * | 3/1996 | Beck et al. | .................... 600/220 |
| 5,509,893 A * | 4/1996 | Pracas | ............................ 600/224 |
| 5,813,855 A | 9/1998 | Crisio, Jr. | |
| 5,997,474 A | 12/1999 | Batchelor | |
| 6,004,265 A * | 12/1999 | Hsu et al. | ...................... 600/223 |

(Continued)

FOREIGN PATENT DOCUMENTS

| | | | | |
|---|---|---|---|---|
| DE | 9209244 U | * | 10/1992 | ............... A61B 1/32 |
| DE | 9209244 U1 | | 10/1992 | |
| WO | 96/28083 A1 | | 9/1996 | |
| WO | 2004/039252 A1 | | 5/2004 | |

*Primary Examiner* — Ellen C Hammond
*Assistant Examiner* — Stuart S Bray
(74) *Attorney, Agent, or Firm* — Brooks Kushman P.C.

(57) ABSTRACT

The present invention provides a speculum including a body, an opening, a first blade pivotably secured to the body and a second blade that is integral with the body. The blades are located at opposed sides of the opening. The first blade is movable between a first retracted position in which it lies adjacent to the second blade and a second extended position in which it is spaced apart from the second blade. A mechanism is also provided to move the first blade from the first position to the second position. When the first blade is in the extended position, there is an inspection channel formed that extends through the opening and between the blades. The mechanism for moving the first blade is preferably located substantially outside the periphery of the opening when the first blade is in the extended position.

14 Claims, 9 Drawing Sheets

(56) References Cited

U.S. PATENT DOCUMENTS

| | | | |
|---|---|---|---|
| 6,174,282 B1 * | 1/2001 | Tan | 600/224 |
| 6,287,251 B1 * | 9/2001 | Tan | 600/224 |
| 6,425,295 B1 | 7/2002 | Meginniss | |
| 6,450,952 B1 | 9/2002 | Rioux | |
| 6,712,761 B2 * | 3/2004 | Borodulin et al. | 600/184 |
| 7,658,712 B2 * | 2/2010 | Klaassen et al. | 600/220 |
| 2002/0016528 A1 * | 2/2002 | Tan | 600/224 |
| 2002/0156350 A1 | 10/2002 | Nieto | |
| 2003/0176772 A1 * | 9/2003 | Yang | 600/220 |
| 2003/0225313 A1 * | 12/2003 | Borodulin et al. | 600/135 |
| 2004/0054260 A1 * | 3/2004 | Klaassen et al. | 600/220 |
| 2005/0113644 A1 | 5/2005 | Obenchain et al. | |
| 2006/0122463 A1 | 6/2006 | Klaassen | |
| 2006/0293567 A1 * | 12/2006 | Borodulin et al. | 600/220 |
| 2007/0073112 A1 * | 3/2007 | Holmes | 600/225 |

* cited by examiner

SPECULUM

CROSS-REFERENCE TO RELATED APPLICATIONS

This application is the U.S. national phase of PCT Application No. PCT/GB2006/002310 filed Jun. 22, 2006 which claims priority to European Application No. 05253889.9 filed Jun. 22, 2005, the disclosures of which are incorporated in their entirety by reference herein.

TECHNICAL FIELD

This invention relates to a speculum suitable for example for performing cervical smear tests.

BACKGROUND ART

Cervical cancer is the second most common cancer in women worldwide and currently approximately a quarter of women with the disease are under the age of 35. As with all cancers, early detection and treatment results in a greater chance of successful treatment. Cervical smear tests have proven to be an effective method for detecting precursor lesions of cervical cancer. To conduct such a test, a sample of cells is taken using a spatula or brush to remove the top layer of cells from the cervix. The cells obtained are then 'smeared' onto a glass slide, fixed with a preservative solution and sent to a laboratory for examination. It is recommended that women have a smear test every 3 years. Tests are currently performed by nurses, doctors and other qualified health practitioners.

However, the smear test is not fulfilling its potential, as uptake by women is lower than desirable and also many women delay taking the test so that the interval between tests is longer than recommended. Factors involved in not taking, or delaying, a test include the stress of having such a test done and women being too busy to arrange and attend an appointment. Performing the test also takes up lots of health practitioner time, presenting a significant drain on the health service. If a sample is deemed to be inadequate, for example due to the presence of blood or an insufficient number of cells, a second smear test needs to be performed.

A speculum is a device used by a health practitioner to open the vagina to assist in gaining access to the cervix; it is usually made of plastic or metal and has two blades, connected by a hinge mechanism and handles to move the blades apart. Thus the blades are moved between an open and closed position by means of a scissor mechanism and may be locked into an open position by a screw thread. The speculum is also used for internal examinations. It is designed for use by a medical practitioner on a patient. The handles are shaped and positioned for use by the medical practitioner, making the device awkward, if not impossible, for the patient herself to hold and operate it. The handles may also restrict the space the health practitioner has when obtaining the sample or performing an internal examination. Further, both hands are required to operate the device.

Currently it is the norm to use an electric lamp having a directable lighting source located behind the health practitioner to provide illumination for the examination or to collect the cervical sample. The health practitioner can therefore obscure the light and cast a shadow on the patient.

WO2004/039252 discloses a vaginal speculum wherein the handle may be disconnected from the blade module once the blades have been inserted in to the vagina and are locked in an open position.

Other designs of specula also exist, such as a surgical speculum with four blades, as described in US2005113644.

WO96/28083 discloses a speculum having four blades that are each held in a housing having a circular opening. The blades are spaced around the opening and they are pivotable with respect to the housing to move the tips of the blade outwards and so open an inspection channel through the speculum that includes the circular opening. The axis about which the blades pivot is located part of the way along the blade length and the inner end of each blade is in contact with a cam ring that is rotatable around the opening. The cam ring has cam surfaces that engage the inner ends of the blades to move them inwards and so pivot the blades about the axis and move the tips of the blades outwards to open the inspection channel. The patent requires a retaining ring to hold the blades in place. Thus the device requires a large number of pieces that have to be fitted together and hence is both expensive to make and to assemble, particularly for a disposable item.

U.S. Pat. No. 5,509,893 discloses a speculum having at least two dilator blades that are each held between an annular support member and a collar so that each blade can be pivoted about an axis part of the way along its length. The support member has a circular opening and the blades are spaced around the opening. When the tips of the blades are pivoted outward, an inspection channel is opened through the speculum that extends through the circular opening and the space between the blades. A cam ring that is rotatable around the opening and has a cam surface engages the inward part of the blade, i.e. away from the tip, and the rotation of the ring causes the cam surface to pivot the blades. The cam ring is held in place by a ratchet and pawl arrangement. The device requires a large number of pieces that have to be fitted together and hence is both expensive to make and to assemble, particularly for a disposable item.

One of the aims of both WO96/28083 and U.S. Pat. No. 5,509,893 is to make a disposable speculum that can be used once and then thrown away. An important aspect of the design of disposable medical item is that it must be made as cheaply as possible, while still fulfilling its function. Nevertheless, even with a two-blade version of the speculums described in these two specifications, the devices must be made using a minimum of five separate pieces and assembly of the pieces is time-consuming and fiddly and therefore the speculums are expensive.

DISCLOSURE OF THE INVENTION

The invention is set out in the claims.

In general terms, the present invention provides a speculum with two blades attached to a device body and an inspection opening; the blades can be moved from a closed or retracted configuration to an open, extended configuration. In the closed configuration, the blades extend in the same general direction, alongside and opposite each other and is suitable for the insertion of the speculum. In the open or extended configuration, which is used when collecting a cervical cell sample, the blades are separated from each other. The two blades preferably have a concave shape and taper towards their far ends, thereby forming a generally conical external shape and an internal space that can protect a cervical sample collector from contamination during insertion or removal from the vagina.

One blade is pivotally connected to the device body and the other is integral with the device body. The first blade is pivotally connected to the body of the device by an opposed pair of hinge pins that engage in corresponding sockets. The use of an integral second blade and the use of the pin-and-socket connection to provide the pivotal connection of the first blade means that the speculum of the present invention can be made out of only three components as compared to a minimum of five in each of WO96/28083 and U.S. Pat. No. 5,509,893. It can also be assembled quickly and cheaply by securing the cam in the body and snap connecting the first blade using the pin and socket connection. Thus, in comparison to a two-blade speculum of WO96/28083 or U.S. Pat. No. 5,509,893, the speculum of the present invention can be manufactured much more cheaply.

The mechanism for opening the speculum, i.e. moving the blades to the open, extended position, may include a ring having a cam surface that is rotatable along a path that lies outside the opening in the device body; as it is rotated, the cam surface directly or indirectly engages the pivotable blade and moves it to the open position. The ring may be held by a groove-and-pin connection similar to a bayonet mechanism. The ring may include a handle extending away from the opening in the device body, enabling the user to rotate the ring. This design of the handle on the ring is suitable for use by right and left handed users. The handle can be arranged such that it does not obstruct a visual pathway through the opening in the device body and extending between the blades when they are in the open position since the handles are preferably located outside the opening in the device body and point away from the centre of the ring.

Due to the design of the moveable cam, the mechanism can remain in an open position without a locking mechanism.

The device body may also include an attachable a mirror, which may be rotated to a suitable angle to assist the user to manipulate the sampling device to obtain a sample of cervical cells. Instead of a mirror, a camera may be used to produce an image of the cervix in use.

One of the blades, preferably the fixed blade, preferably comprises a holder, e.g. a snap fit mechanism, on its inner surface to hold a cervical sample collector, e.g. a brush. The sample collector can thereby be preloaded into the speculum before insertion, to simplify the procedure and reduce the risk of contamination of the collector, and consequently of the sample.

The sample collector preferably includes a sample collecting head attached to a rod and a light source, e.g. a removably attachable light emitting diode (LED), that directs light to the sample collecting head. Conveniently, the rod may be transparent and the light source directs light down the rod which acts as a light guide conducting the light towards the collecting head. This has the benefit of aiding visualisation of the cervix when taking the sample of cells. A further benefit of incorporating a light source, e.g. an LED, is to use the light as an indicator when the sample collector is applied against the cervix with the requisite force needed to take a satisfactory sample. Thus the sample collector may include a pressure sensor that alters the light emitted by the light source (e.g. it might change colour or pulse) when the collector head is applied against the cervix with the required pressure, thereby alerting the user. Instead of altering the emitted light, other visual or audible alerts could be given that indicate when the required pressure has been applied. This increases the likelihood of obtaining a good sample.

Using the present invention, the user is able to obtain a cervical cell sample herself, without the need for a health practitioner, in the comfort and privacy of her own home and at a time of her own choosing. The speculum and sample collector are easy to use. Thus there is no need to arrange an appointment and visit a doctor's surgery, which must be planned around the menstrual cycle. The whole process of obtaining a cervical smear test result is thereby speeded up and it is likely that more women will take a smear test at the appointed time, thereby increasing the number of women in whom cancer is detected at an early stage and for whom treatment could be successful.

BRIEF DESCRIPTION OF THE FIGURES

A specific embodiment of the invention will now be described by way of example with reference to the accompanying drawings:

FIG. 9 show schematically the operation of the speculum and sample collector of FIGS. 1 to 8 in the collection of cervical cell samples.

DETAILED DESCRIPTION AND BEST MODE FOR CARRYING OUT THE INVENTION

Figure 1:
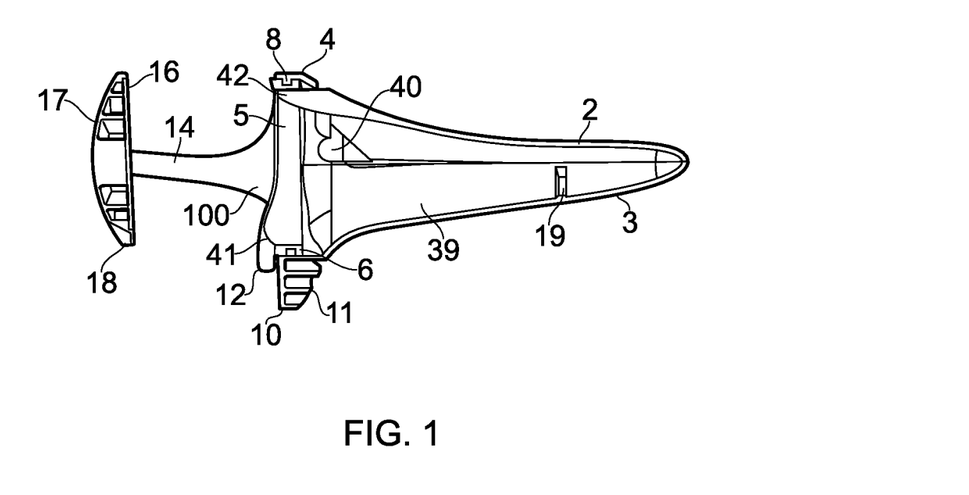
FIGS. 1 and 2 are vertical cross sectional views of the speculum of the present invention in the closed position and open position, respectively.
Figure 2:
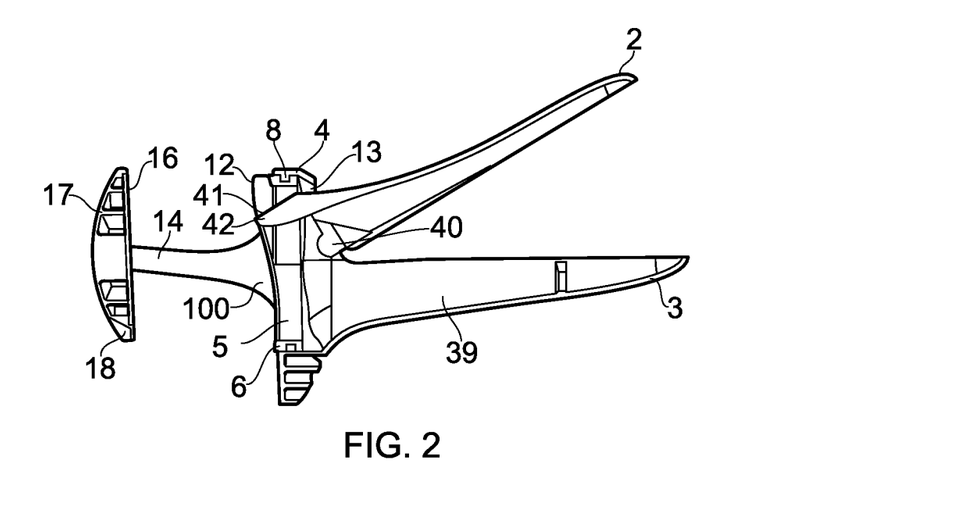
Figure 3:
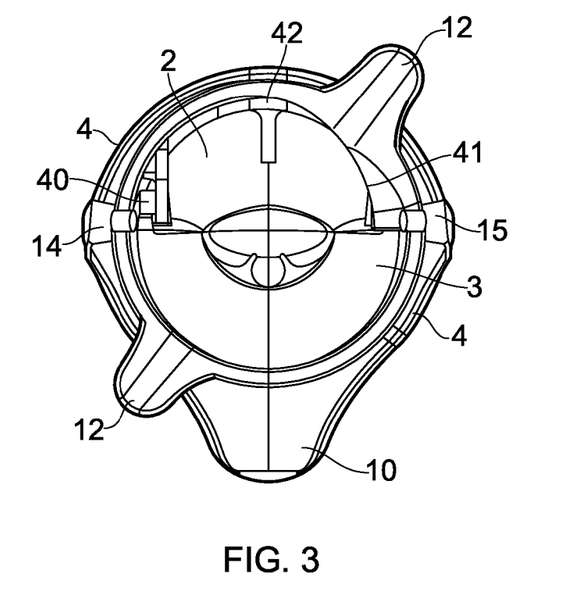
FIGS. 3 and 4 are front views of the speculum of the present invention in the closed position and open position, respectively.
Figure 4:
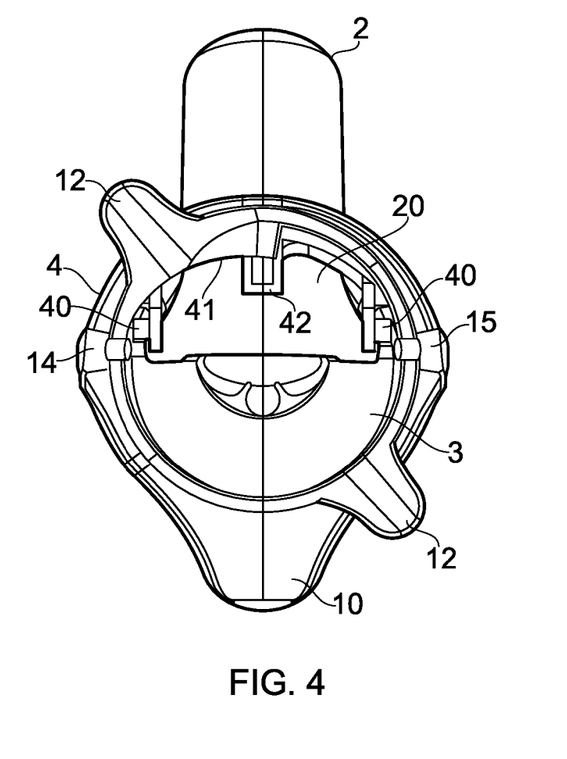
Figure 5:
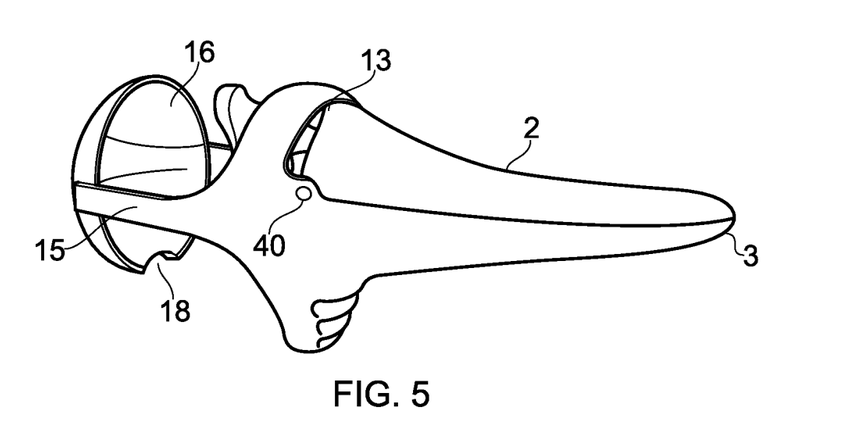
FIGS. 5 and 6 are perspective views of the speculum of the present invention.

Referring initially to FIGS. 1 to 4, there can be seen a speculum 1 in accordance with the present invention; in FIGS. 1 and 3 it is in a closed position and in FIGS. 2 and 4 it is in an open position.

The speculum has a device body 100 that includes an outer annulus 4 and two blades 2, 3 that are connected to the body 100. The blades are opposed to each other and extend parallel to each other. The first blade 2 carries a pair of opposed hinge pins 40 that engage in corresponding sockets in the device body 100, whereby the first blade is pivotally connected with respect to the body 100. The second blade 3 is fixedly connected to the body and indeed integral with it.

The inside surfaces of the blades 2, 3 are generally concave and so define an internal space 39, while their outer surfaces are convex and taper towards the end of the speculum so that together they form a conical shape. When in the closed position, the edges of the two blades are in register. The blades are preferably shaped in such a way to provide the most comfortable fit and therefore the surfaces of the two blades need not be tapered in an identical manner.

The outer edge of the annulus 4 has a diameter of about 4-6.5 cm and the inner surface of the annulus 4 is about 3.5-6.3 cm in diameter. The blades 2,3 are approximately 8-14 cm long, preferably about 9-12 cm long. The outer diameter of the blades at the annulus end is about 4-6.5 cm, depending on the outer diameter of the annulus 4. The outer diameter of the blades at the end furthest from the annulus 4 is about 2-2.5 cm.

The device body 100 includes a grip 10, which is integrally formed with the outer ring 4, to assist in insertion of the device into the vagina and its correct placement. Preferably the side of the grip 10 facing towards the blades 2,3 is provided with a ribbed surface 11 to maintain a substantial wall thickness.

An inner ring 5 is provided that fits within the outer annulus 4. The inner ring 5 has a groove 6 on its outer peripheral surface 7 and the inside surface 9 of the outer ring 4 has a number of projections 8 which engage in the groove 6 and allow the inner ring 5 to turn within the annulus 4. The inner ring 5 is provided with channels perpendicular to the grooves 6 that allow, in the manner of a bayonet connection, the inner ring to be fitted onto the projections. In order to limit the angle through which the inner ring 5 may be turned, the groove 6 is in the form of a number of evenly spaced grooves that each extends only part of the way round the inner ring 5; for example, there may be three grooves each extending 90° around the inner ring to limit the angle through which the second ring may be turned to 90°.

The inner ring 5 preferably has at least one handle 12 to assist in rotating it and, in the embodiment shown in the drawings, it has two handles 12 opposite each other. The handles mimic the shape of the grip 10 on the speculum, and extend away from the centre of the ring 5.

The inside surface of the inner ring 5 is not circular but includes a cam surface 41. One end 42 of the pivoted blade 2 extends backwards so that it lies within the inner ring and engages its inner surface. When the speculum is closed (see FIG. 1), the cam does not engage the end 42; however, when the second ring 5 is rotated, the cam surface 41 engages the end 42 of the pivoting blade 2, causing it to pivot about the pivot pins 40 and so separate the blades 2,3. FIGS. 2 and 4 show the blades 2,3 in a fully opened position. The inner ring 5 can be turned in the opposite direction to allow the pivoted blade 2 to move back towards the fixed blade 3 and hence close the speculum. The arrangement is such that, by turning the inner ring 5 by 90°, the speculum can be opened. A slot 13 is provided in the body 100 to allow the pivotal movement of the first blade 2.

The cam angle of the cam surface 41 and the friction of the end 42 against the cam 41 and the friction of the inner ring 5 within the outer ring 4 keeps the pivoted blade 2 in its open position without a locking mechanism.

The speculum preferably has a pair of opposed arms 14,15 for removably holding a mirror 16. The mirror 16 is round and its backing 17 is preferably dome-shaped for ease of handling during the procedure of obtaining a sample. The mirror may have a groove 18, which provides a guide for positioning a sample collector, as described below. The mirror arms 14,15 are approximately 5-10 cm long, preferably 7-9 cm long.

Figure 6:
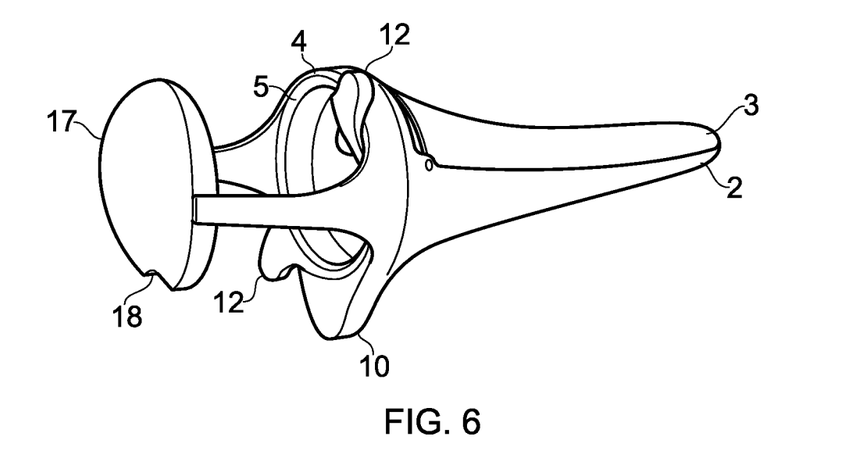

As can be seen from FIG. 4, a central inspection channel 20 is created through the opening in the annulus and ring 4,5 and extends between the blades 2,3 when the speculum is opened. As can be seen in FIGS. 4 and 6, the handles 12 of the inner ring 5 extend outwards away from the centre of the ring and do not obscure the inspection channel 20.

Figure 7:
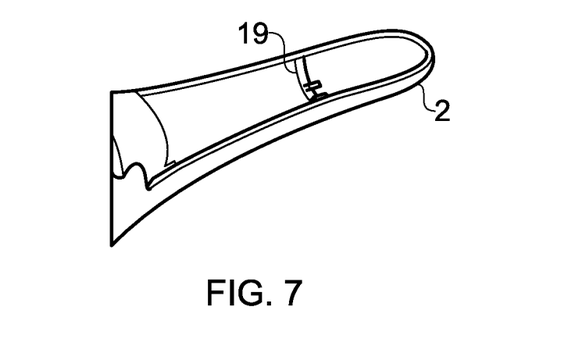
FIG. 7 is a perspective view of the lower, fixed blade showing a clip for a sample collector.

FIG. 7 shows the inside surface of the fixed blade 3 which has a clip 19 on its inner surface to hold a cell sample collector in place; the collector contains a brush head and will be described in further detail later. However, here it should be noted that there is sufficient space within the inside cavity of the blades and between the clip 19 and the end of the blade 3 to accommodate a brush head of the sampling collector.

As indicated above, the speculum is intended for use in conjunction with a device for collecting a sample of cells from a woman's cervix, which in the illustrated embodiment is a brush 50 (see FIG. 9 and the description below) provided at the lower end of a rod 33 made of a transparent material, e.g. polycarbonate. The brush head used for obtaining a sample is of a standard type used for taking cervical smears and is provided in a sterile packaging 51.

Figure 8:
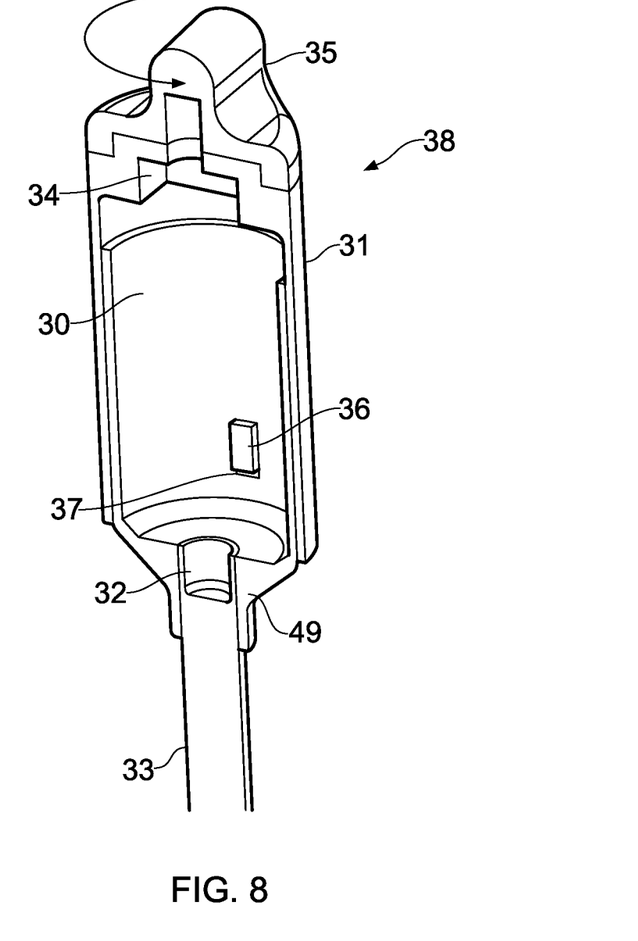
FIG. 8 is a partial cross-sectional view of part of a sample collector.

The upper end of the rod 33 is held by friction in a socket 49 in the base of a handle 38, see FIG. 8. An LED casing 32 is formed in the end of the rod located within the socket 49.

The handle 38 includes a battery casing 30, 31 that consists of an inner shell 30 and an outer shell 31 that can move in the axial direction relative to each other. A small projection 36 on the outer casing is held in a slot 37 provided on the inner casing; the projection 36 can slide along the slot 37 in order to allow limited axial movement but prevent rotational movement between the outer and inner casing shells 30,31. The inner shell 30 accommodates a battery (not shown) to power an LED (not shown) installed in the LED casing 32 to produce light that is directed along the rod 33, acting as a light guide, to provide light at the lower end of the rod; the ability to provide illumination in the region of the collecting brush 50 assists in positioning the brush to collect a cervical cell sample. A switch knob 35 is provided to turn the LED on and off.

A pressure-sensitive switch (not shown) is provided in a switch casing 34 at the top end of the handle 38, i.e. at the opposite end to the LED casing 3. A force tending to push the rod 33 upwards into the handle, will cause the inner battery casing shell 30 and the battery to be moved upwardly within the outer casing shell 31 by an amount dictated by the length of the slot 37; equally this movement can be thought of as a downward movement of the outer casing shell 31 of the handle 38 with respect to the rod 33 and the inner battery casing shell 30. When the force exerted by the battery on the switch exceeds a threshold value, the switch is closed and the closing of the switch causes the LED to change its operation (see below). The threshold pressure is set at the pressure that the brush must exert on the cervix to get an acceptable cell sample. Thus the alteration in the operation of the LED indicates to the user that this pressure is being applied.

Figure 91:
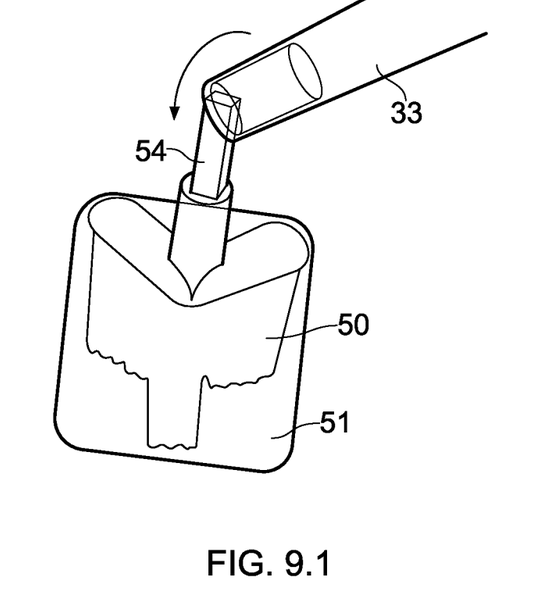

The operation of the speculum and brush will be described by reference to FIG. 9. A brush head 50 is provided in a sterile cover 51; the brush includes a connector 54 for push-fitting the brush onto the rod 33. The cover 51 is opened (FIG. 9.1) and the connector 54 is revealed and is pushed into a socket at the end of the rod, which holds the brush firmly on the end of the rod. The handle 38 will already have been pushed onto the other end of the rod 33; the brush, rod and handle together form a cervical sample collector 47. The cover 51 is not removed from the brush at this stage.

Figure 92:
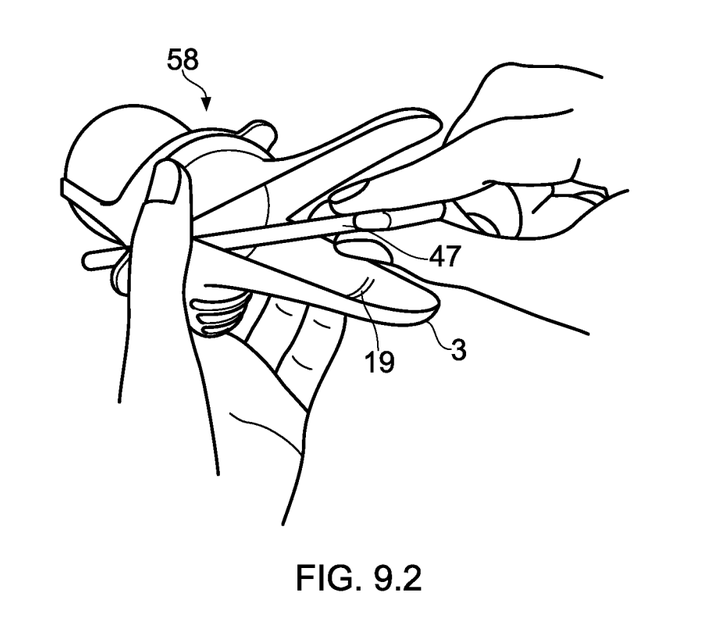
Figure 93:
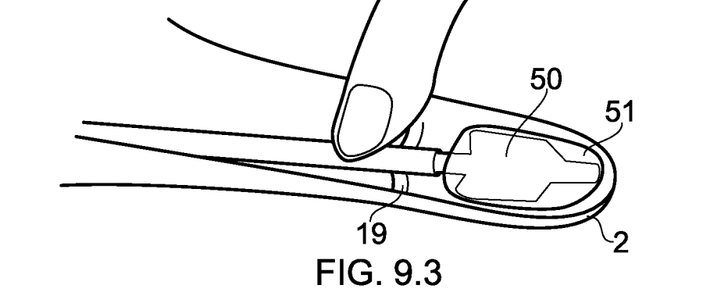
Figure 94:
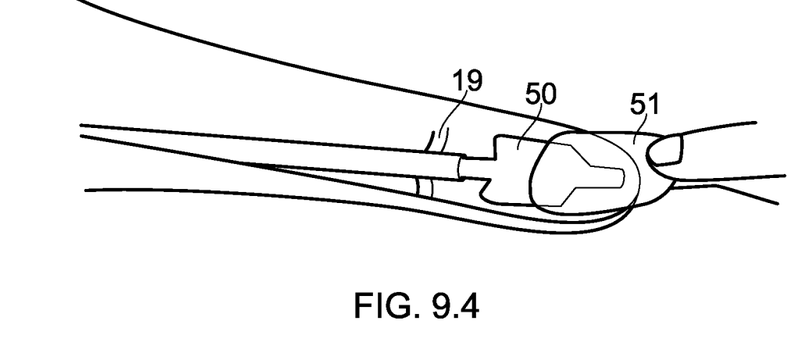

The sample collector 47 is then placed (FIGS. 9.2 and 9.3) into the speculum 58 and is held in place by the clip holder 19 on the fixed blade 3. The sterile cover 51 is then removed from the brush head (FIG. 9.4).

Figure 95:
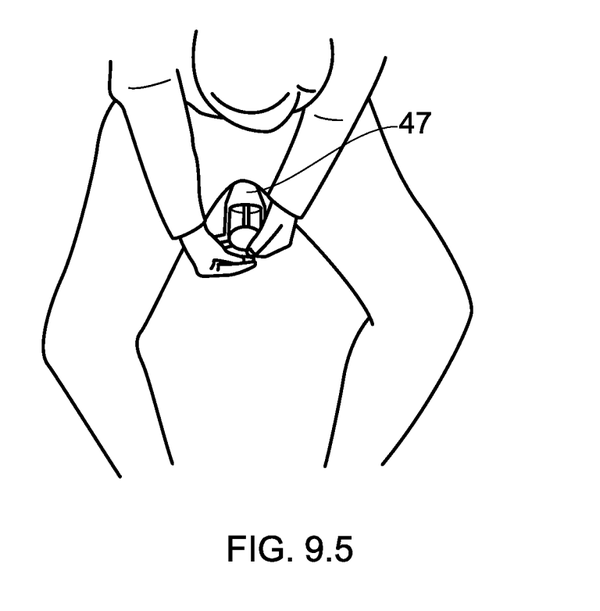
Figures 96, 97:
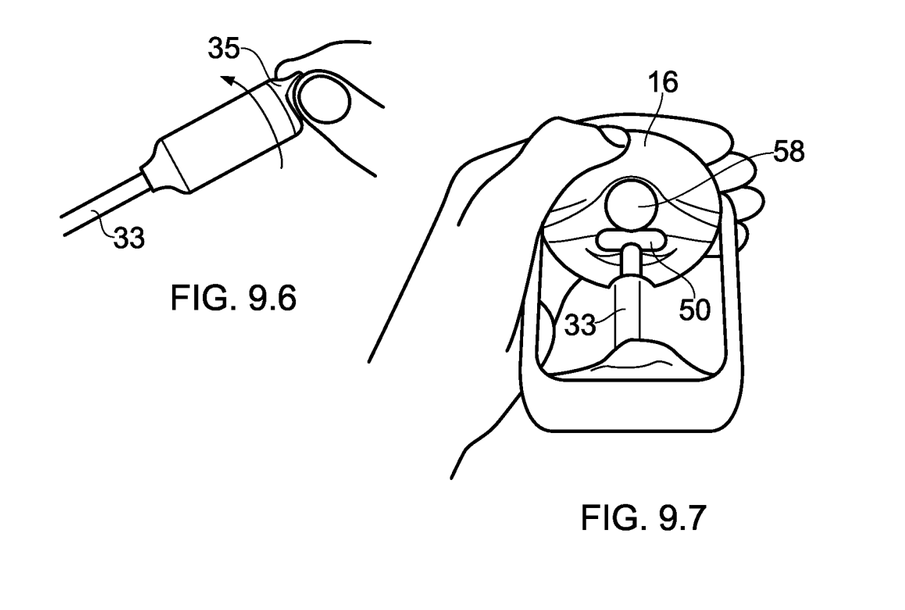

The speculum is inserted into the vagina (FIG. 9.5) and the blades of the speculum are opened by rotating the handles 12 in a clockwise direction. The handle 38 of the sample collector 47 projects though the end of the speculum and can be manipulated to remove the rod 33 from the holder clip 19 in the speculum. The LED can be turned on (FIG. 9.6) by turning the switch knob 35.

Figure 98:
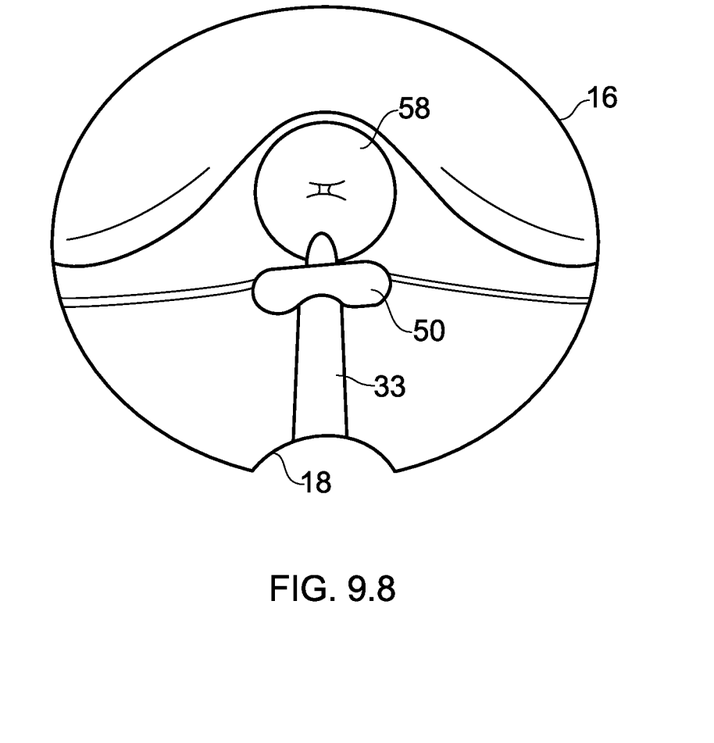
Figure 99:
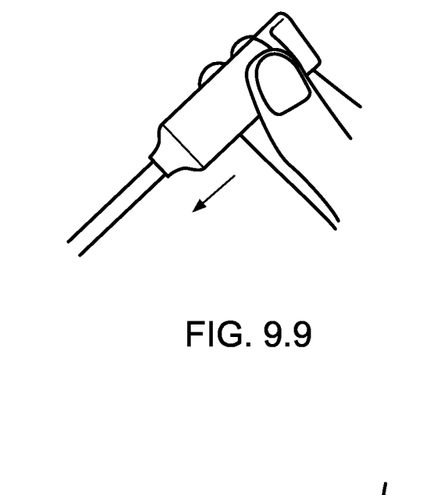

The mirror 16 is moved as required so that the user can see her cervix 58 (FIG. 9.7). Using the mirror, the tip of the brush 50 is directed at the centre of the cervix 58 (FIG. 9.8). In manipulating the sample holder 47, the handle 38 is held and pushed axially to apply the brush against the cervix; the rod 33 can be steadied by engaging it in the groove 18 in the mirror. When the brush is applied with the required pressure to take a cell sample, the battery is pressed against the switch in the handle 38 (FIG. 9.9), as described above, with sufficient pressure to close the switch and cause an alteration in the operation of the LED. In one embodiment, the LED normally transmits a steady light and it changes to a flashing light when the correct pressure is exerted. Alternatively, the colour of the light emitted by the LED changes, for example a RGB (red-green-blue)-type LED could be used and the emitted white light could for example change to red light. In a further embodiment, the light intensity could increase or decrease once a sufficient pressure is exerted on the sampling brush. Alternative audible, tangible or visible indications may be given instead of altering the operation of the LED.

Figure 910:
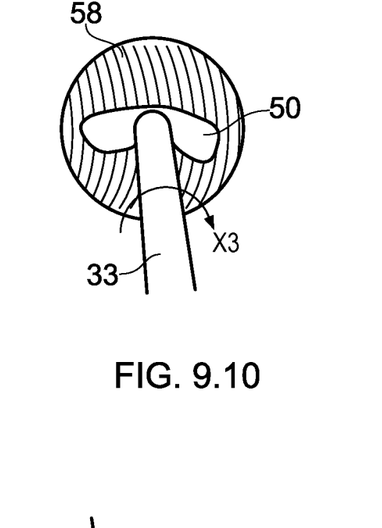

On observation of the change of LED operation, the cell sample is taken by turning the handle 38, and hence the brush 50, while maintaining the pressure against the cervix at the required level, which is sufficient to cause the brush bristles to flex, as shown (FIG. 9.10). Two revolutions of the brush will generally be sufficient to collect the required cells.

Figure 911:
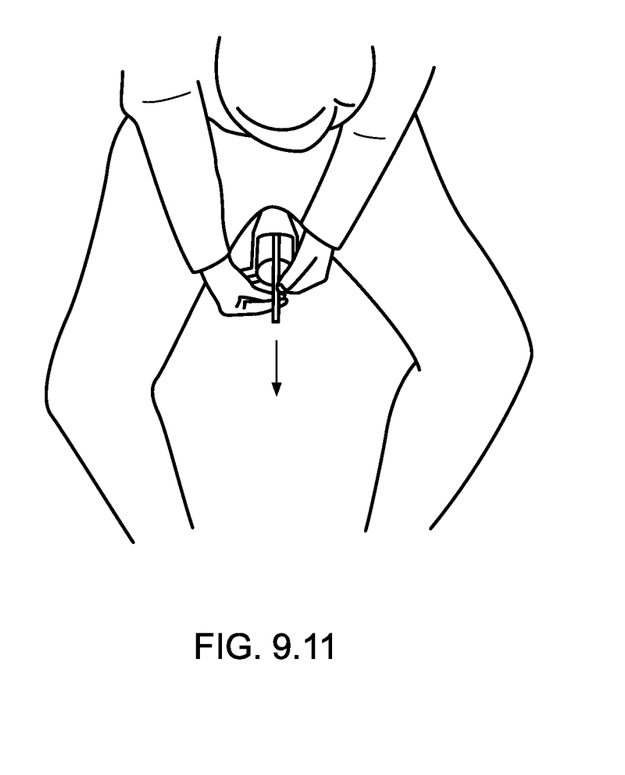
Figure 912:
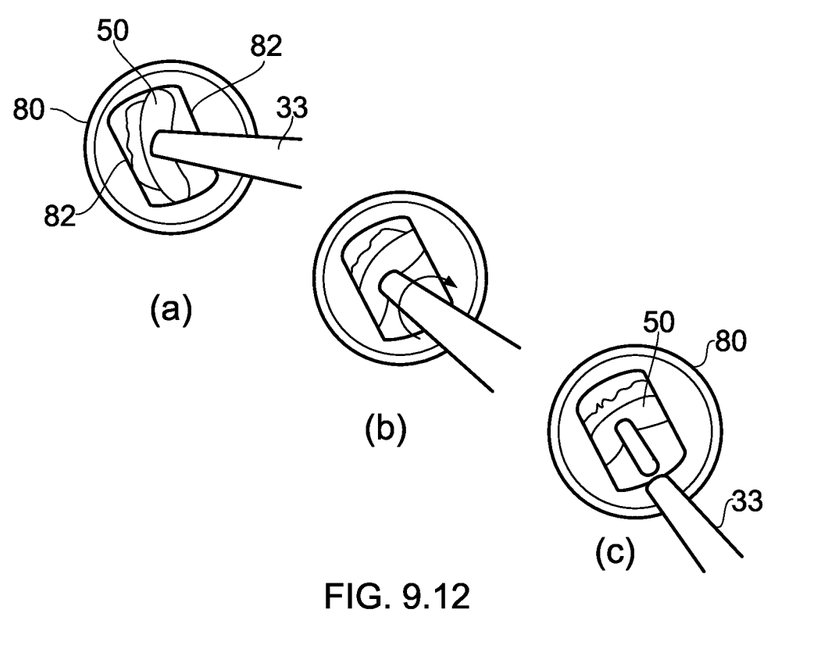

The collector 47 is then removed from the vagina, taking care not to touch the brush against the vagina walls (FIG. 9.11). The LED can then be switched off by rotating the switch knob 35. After removal, the brush is placed into a cylindrical vial 80 (FIG. 9.12a, which shows the vial from above) that has a diameter greater than the width of the brush 50. There are a pair of opposed internal ridges 82 inside the vial located part of the way down the vial wall. These ridges are spaced apart by less than the width of the brush 50 so that the brush can be inserted into the vial with the brush lying parallel to the ridges and then it is twisted through 90° (FIG. 9.12b) so that the brush is caught under the ridges and the rod 33 can be pulled off the brush head, leaving the brush head inside the vial (FIG. 9.12c). This eliminates the need to detach the brush head by hand, thereby avoiding the risk of sample contamination. The vial is then sent off to a laboratory for analysis (FIG. 9.11). The rod 33 and the handle 38 can be sterilised and reused. Instead of a vial, any other sample carrier, e.g. a microscope slide, may be provided.

The speculum is preferably manufactured by injection moulding in 3 pieces, that is to say the device body 100 (including the fixed blade 3), the pivoting blade 2 and the inner ring 5. As materials for the speculum, any hard, rigid plastic suitable for medical use would be acceptable, e.g. ABS (Acrylonitrile Butadiene Styrene), styrene, polycarbonate, PVC, acrylic and ABS-polycarbonate mixes.

The speculum of the present invention would usually be supplied as part of a kit. The kit would contain the speculum and additionally at least one brush head in a sterile, protective packaging; a rod 33 for use as a brush handle; the LED and battery unit; the mirror; and at least one vial, containing alcohol solution to preserve the sample, and with ribs to engage the brush head. The kit would also contain instructions for use as a leaflet and/or a compact disc. Optionally the kit would also contain a lubricating agent.

Certain parts of the kit could be reusable, for example the speculum, the rod, the LED, the battery and the mirror. The rod and speculum can be boiled to sterilise them after use. Kits containing a replacement brush head and vial, containing preservative solution, for example 95% ethanol, could be sold separately. Alternatively the speculum and rod could also be intended for single use.

The speculum of the present invention need not be exclusively for home use. If the mirror is not attached to the speculum, the speculum would also be suitable for hospital or general medical use for example for inspections, aiding surgery and also for health practitioners taking cervical smear samples. The shape of the handles 12 means that there is no restriction on visibility and also allows the health practitioner complete freedom of movement during a procedure.

It can be seen that the speculum of the present invention can be made with only 3 parts (4 including the mirror) and it is easy and cheap to assemble, as compared to the prior art; there is no need to provide multiple pivotable blades around an opening, which makes the assembly of prior art speculums time consuming and expensive.

The invention claimed is:

1. A speculum comprising:
a body;
an opening;
a first blade and a second blade that are each secured to the body at opposed sides of the opening, wherein the first blade is pivotally secured with respect to the body and movable between a first retracted position in which the first blade lies adjacent to the second blade and a second extended position in which it is spaced apart from the second blade; and
a mechanism configured to move the first blade from the first position to the second position, the mechanism comprising a member that is movable along a path that lies outside the opening and wherein the member is configured to move the first blade from the retracted to the extended position as it moves along the said path,
wherein, when the first blade is in the extended position, there is an inspection channel formed that extends through the opening and between the blades;
wherein the first blade is pivotable with respect to the body and the second blade is integral with the body and wherein the first blade is pivotally connected to the body by an opposed pair of hinge pins that engage in corresponding sockets;
wherein the movable member is provided on a ring that is rotatable along the path that lies outside the opening and wherein said ring has a cam surface;
wherein as the ring is rotated in a first direction by one hand of the user an end of the first blade engages the cam surface to pivot the first blade with respect to the body from the first retracted position to the second extended position; and
wherein as the ring is rotated in an opposite direction by one hand of the user the first blade pivots back to the first retracted position when the end of the first blade does not engage the cam surface.

2. The speculum as claimed in claim 1 wherein the cam surface is defined along an inner race of the ring and includes at least one cam angle, first blade is held in the second retracted position by the interaction of the end of the first blade with the cam angle until the ring is rotated in an opposite direction by the hand of the user.

3. The speculum as claimed in claim 2 wherein the end of the first blade does not contact the cam angle in the first retracted position.

4. The speculum as claimed in claim 1, wherein said path is at least partly circular and extends around the periphery of the opening.

5. The speculum as claimed in claim 1, wherein the opening is formed by the ring.

6. The speculum as claimed in claim 1, wherein said mechanism includes a handle to move the movable member along the path.

7. The speculum as claimed in claim 1, and further comprising a mirror configured to reflect radiation passing along the inspection channel, said mirror optionally being removable.

8. The speculum as claimed in claim 1 wherein the second blade is formed integral with the body such that the second blade is immovable with respect to the body.

9. A speculum for self-sampling by a user, the speculum comprising:
a body defining a central opening;
first and second blades connected to the body at opposed sides of the opening, wherein at least the first blade is pivotally connected to the body and movable between a first closed position in which the first blade lies adjacent to the second blade and a second open position in which the first blade is spaced apart from the second blade, wherein in the open position, an inspection channel extends through the opening and between the first and second blades;

a mirror connected to the body at an end of the channel, the mirror configured to reflect radiation passing along the inspection channel; and a blade opening mechanism including a ring rotatable with respect to the body, the ring having an inner cam surface and a handle, wherein as the ring is rotated in a first direction by one hand of the user an end of the first blade engages the cam surface to pivot the first blade with respect to the body from the first retracted position to the second extended position in order to facilitate self-sampling and inspection by the user.

10. The speculum as claimed in claim 9 wherein the handle extends away from the opening and does not extend into the opening so that the handle does not obstruct the inspection channel when the blades are in the open position.

11. The speculum as claimed in claim 9 wherein the first blade is pivotally connected to the body by an opposed pair of hinge pins that engage in corresponding sockets in the body.

12. The speculum as claimed in claim 9 wherein in the open position, the end of the first blade engages the inner cam surface in the open position and does not engage the inner cam surface in the closed position.

13. The speculum as claimed in claim 9 wherein the second blade is formed integral with the body such that the second blade is immovable with respect to the body.

14. The speculum as claimed in claim 9 wherein the cam surface is defined along an inner race of the ring and includes at least one cam angle, first blade is held in the second retracted position by interaction of the end of the first blade with the cam angle until the ring is rotated in an opposite direction by the hand of the user.

\* \* \* \* \*